United States Patent [19]
Toh et al.

[11] Patent Number: 6,088,108
[45] Date of Patent: Jul. 11, 2000

[54] LEADED COMPONENTS INSPECTION SYSTEM

[75] Inventors: Peng Seng Toh, Parc Oasis; Chiat Pin Tay, Singapore; Poh Loy Chow, Singapore; Peh Kwan Han, Singapore, all of Singapore

[73] Assignee: Hewlett-Packard Company, Palo Alto, Calif.

[21] Appl. No.: 09/205,852

[22] Filed: Dec. 4, 1998

[30] Foreign Application Priority Data

Aug. 27, 1998 [SG] Singapore ............................ 9803329-3

[51] Int. Cl.[7] ..................................................... G01B 11/24
[52] U.S. Cl. .......................................... 356/375; 356/237.1
[58] Field of Search ..................................... 356/375, 376, 356/399–401, 237.1; 382/106, 141, 152

[56] References Cited

U.S. PATENT DOCUMENTS

| | | | |
|---|---|---|---|
| 4,553,843 | 11/1985 | Langley et al. | 356/375 |
| 5,311,304 | 5/1994 | Monno | 348/87 |
| 5,528,371 | 6/1996 | Sato et al. | 356/372 |
| 5,663,799 | 9/1997 | McAulay et al. | 356/398 |
| 5,909,285 | 6/1999 | Beaty et al. | 356/394 |

*Primary Examiner*—Frank G. Font
*Assistant Examiner*—Tu T. Nguyen
*Attorney, Agent, or Firm*—Edward Y. Wong

[57] ABSTRACT

An optical inspection system for determining the positional information of a leaded electrical component with respect to a reference is provided. The system has a datum placed in proximity to leads of the leaded electrical component that provides the reference. It also has a light source that provides light that impinges on the leads and the datum so that the images of points on the leads and the datum are formed along various optical paths. The light source is set up so that a point on the leads and a point on the datum will lie in the same plane as their images along at least two optical paths that cross each other at an angle. In addition, the system has an imaging subsystem that captures the images along the two optical paths. The subsystem also correlates and analyses the captured images to provide positional information of the point on the leads with respect to the point on the datum.

20 Claims, 5 Drawing Sheets

LEADED COMPONENTS INSPECTION SYSTEM

FIELD OF INVENTION

The invention relates generally to the inspection of leaded electrical components. In particular, it relates to an inspection system for determining the lead dimensions of leaded electrical components at very high speeds.

BACKGROUND OF THE INVENTION

The production of leaded electrical components such as low pin-count Integrated Circuit (IC) components, for example the SOT23 (Small Outline Transistor for SOT), at very high speeds usually involves the use of rotary-indexed machines. Each IC component usually has three to six leads distributed on two of its opposing sides. During production, such IC components are held by their top surfaces by a pickup head on the rotary-indexed machines using vacuum suction. Each IC component is then indexed through different stations for different processes such as trimming, forming, electrical testing, marking and inspection processes. After processing, the IC components are transferred to a taping station where the IC components are adhered to a tape; this is known as the taping process. The tape is subsequently wound onto a reel for bulk packaging. For process and quality control purposes, the geometry of these IC components is usually inspected during their production.

In conventional ways of inspecting low pin-count IC components using rotary-indexed machines at very high speeds, implied measurement methods are typically involved. Such methods include the acquisition and analysis of a single view on the IC component. The acquisition of this single view is done with a camera that captures an image of the top of an IC component at the taping station. This type of top-view implied measurement method is used to infer defects such as bent leads from the length of the leads. The implied measurement method, however, is insensitive and thus gives inaccurate results when used. This implied measurement method is only effective in detecting leads on IC components that are distorted to a significant degree. On the other hand, if strict tolerance is imposed on the implied measurement method, a very high and impractical rejection rate will be obtained.

Other new and innovative solutions have also been proposed, one of which involves the capture of two orthogonal views of an IC component in a single image for analysis. The first view comprises the side view of the IC component, which may be effectively analyzed to provide curled leads and other types of information. The second view is orthogonal to the first view, and usually comprises the bottom view of the IC component. This second view enables lead length, pitch, width, terminal dimension and other types of information regarding the IC component to be determined.

Although the exemplified proposed solution allows the complete geometry of low pin-count IC components to be inspected, it has disadvantages. In this proposed solution, the first and the second views are provided by light that is reflected from the relevant surfaces on the IC components. Hence the quality of the captured image is subject to variations of the lead surface, the IC component package surface, and ambient light. The accuracy and reliability of the results may thus be compromised. Moreover, the lighting setup that provides the light must be changed when the type of IC component under inspection is changed. For example, the lighting setup needs to be tweaked in terms of direction or intensity when a three-lead IC component is changed to a five-lead IC component. Most importantly, however, the coplanarity of the IC component and the standoff of each lead on the IC component cannot be determined using this proposed solution.

Thus, a need exists for an IC component inspection system to measure the coplanarity of the IC component and provide standoff information for each lead on the IC component at very high speeds. The IC component inspection system should also test different types of IC components, each having a different pin-count, without any lighting adjustments.

SUMMARY OF THE INVENTION

The invention provides an optical inspection system for determining the positional information of an object with respect to a reference. The system has a datum placed in proximity to the object that provides the reference. It also has a light source that provides light that impinges on the object and the datum so that the images of points on the object and the datum are formed along various optical paths. The light source is set up so that a point on the object and a point on the datum will lie in the same plane as their images along at least two optical paths that cross each other at an angle. In addition, the system has an imaging subsystem that captures the images along the two optical paths. The subsystem also correlates and analyses the captured images to provide positional information of the point on the object with respect to the point on the datum.

Preferably, the optical inspection system uses one camera to capture the images simultaneously. The system also uses the light source as a backlight so that backlit images of the points on the object and the datum are formed along the various optical paths. It further uses a prism operating in a total internal reflection mode and a mirror to relay the backlit images along the two optical paths into the camera.

The invention advantageously provides an IC component inspection system for measuring the coplanarity of IC components and providing standoff information for each lead on the IC components at very high speeds. The IC component inspection system can also test different types of IC components, each having a different pin-count, without any lighting adjustments.

BRIEF DESCRIPTION OF THE DRAWINGS

The invention will be better understood with reference to the drawings, in which.

DETAILED DESCRIPTION OF THE EMBODIMENTS

Figure 1:
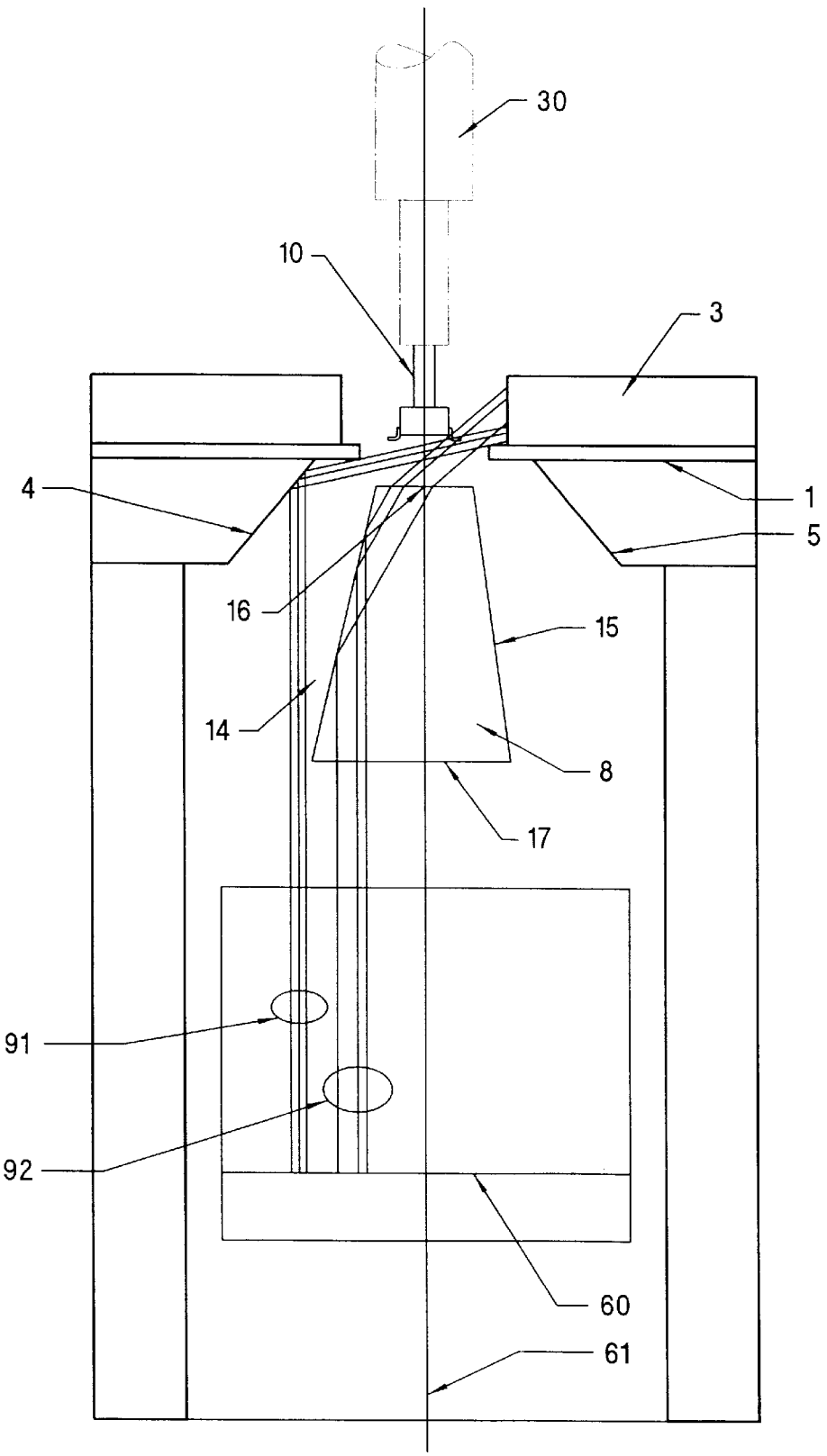
FIG. 1 illustrates a cross-section view of an optical inspection system according to a preferred embodiment of the invention.
Figure 2:
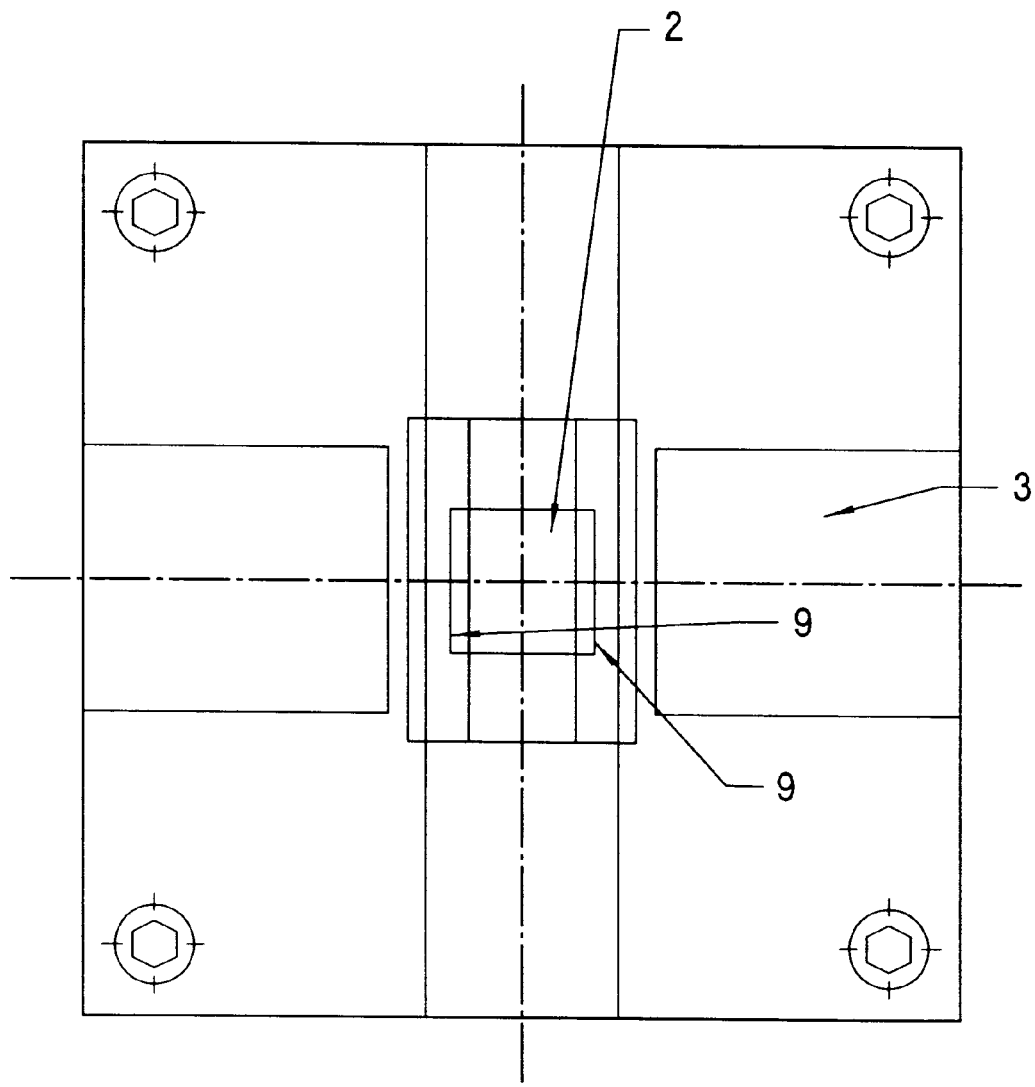
FIG. 2 illustrates a plan view of the optical inspection system of FIG. 1.

Reference is first made to FIGS. 1 and 2 to briefly describe an optical inspection system 11 according to a preferred embodiment of the invention, generally known herein as a "system". The system 11 consists of a datum 1 which has an opening 2 generally known herein as a "window" with two well defined edges 9. The system 11 also consists of two rows of uniform light source 3 positioned on the datum 1 in the proximity of the window 2. Two mirrors 4, 5 are attached to the bottom of the datum 1 and inclined at an angle with respect to the datum 1. The mirrors 4, 5 are also positioned to the sides of the datum 1 and clear of the window 2. Situated below the center of the window 2 is a trapezoidal prism 8. Two internal surfaces 14, 15 on the trapezoidal prism 8 permit total internal reflection for light rays approaching the internal surfaces 14, 15 at certain angles. The light rays projected from the light source 3 enters the trapezoidal prism 8 from a top surface 16 and exits from it through a bottom surface 17. A camera 60 is positioned below the trapezoidal prism 8 to capture images relayed by the mirrors 4, 5 and the trapezoidal prism 8. The camera 60 is further connected to a computer (not shown) for processing and analyzing the captured image.

The operational aspect of the system 11 will now be described with reference to FIG. 1. An electrical component 10, for example a leaded electrical component such as a dual-sided six-lead IC component, for inspection by the system 11 is picked from its top surface with a pickup head 30. The IC component 10 is then positioned over the window 2, with its leads on each side in proximity to each of the datum edges 9, and above the trapezoidal prism 8. As such, the pickup head 30, the IC component 10, the window 2, the trapezoidal prism 8 and the camera 60 are in axial alignment. This axis also coincides with the optical axis 61 of the camera 60.

The optical paths of light impinging the tip of a lead 80 on one side of the IC component 10 will now be traced in order to provide a better description on the operation of the system 11. The light source 3 provides light that impinges on the tip of the lead 80, thereby forming a backlit image of the tip of the lead 80. The image is then projected, crossing the axial plane of the optical axis 61, onto the mirror 4 and is subsequently reflected into camera 60. The optical path taken by such light providing the image will be known as the first optical path 91 herein. The first optical path 91, before undergoing reflection at the mirror 4, subtends a small angle of inclination $\theta_1$ with the top surface of the datum 1, and it is also known as "low oblique path". The light source 3 also provides light that impinges the tip of the lead 80 and projects a backlit image onto the top surface 16 of the trapezoidal prism 8. The image is then projected onto the internal surface 14 on the trapezoidal prism 8 where it undergoes total internal reflection, and out of the trapezoidal prism 8 through the bottom surface 17. Subsequently, the image is projected into the camera 60. The optical path taken by such light providing the image will be known as the second optical path 92 herein and it subtends an angle of inclination $\theta_2$ with the datum 1, which is larger than the angle of inclination $\theta_1$.

Simultaneously, the light source 3 provides light that impinges the datum edge 9 proximal to the tip of the lead 80, thereby projecting the backlit images of the datum edge 9 along the first and second optical paths 91, 92. The mirror 4 and the trapezoidal prism 8 respectively then relay these images into the camera 60.

Hence in a single instance, the camera 60 captures and images, from each of the first and second optical paths 91, 92, the positional relationship between the tip of the lead 80 and the datum edge 9. Other parts of the IC component 10 in relation to the datum edge 9 are also captured and imaged by the camera 60 via the first and second optical paths 91, 92 in the same way. In the same instance, the camera 60 also captures an image of the side on the IC component 10 opposing the side described in the preceding sections.

Figure 3:
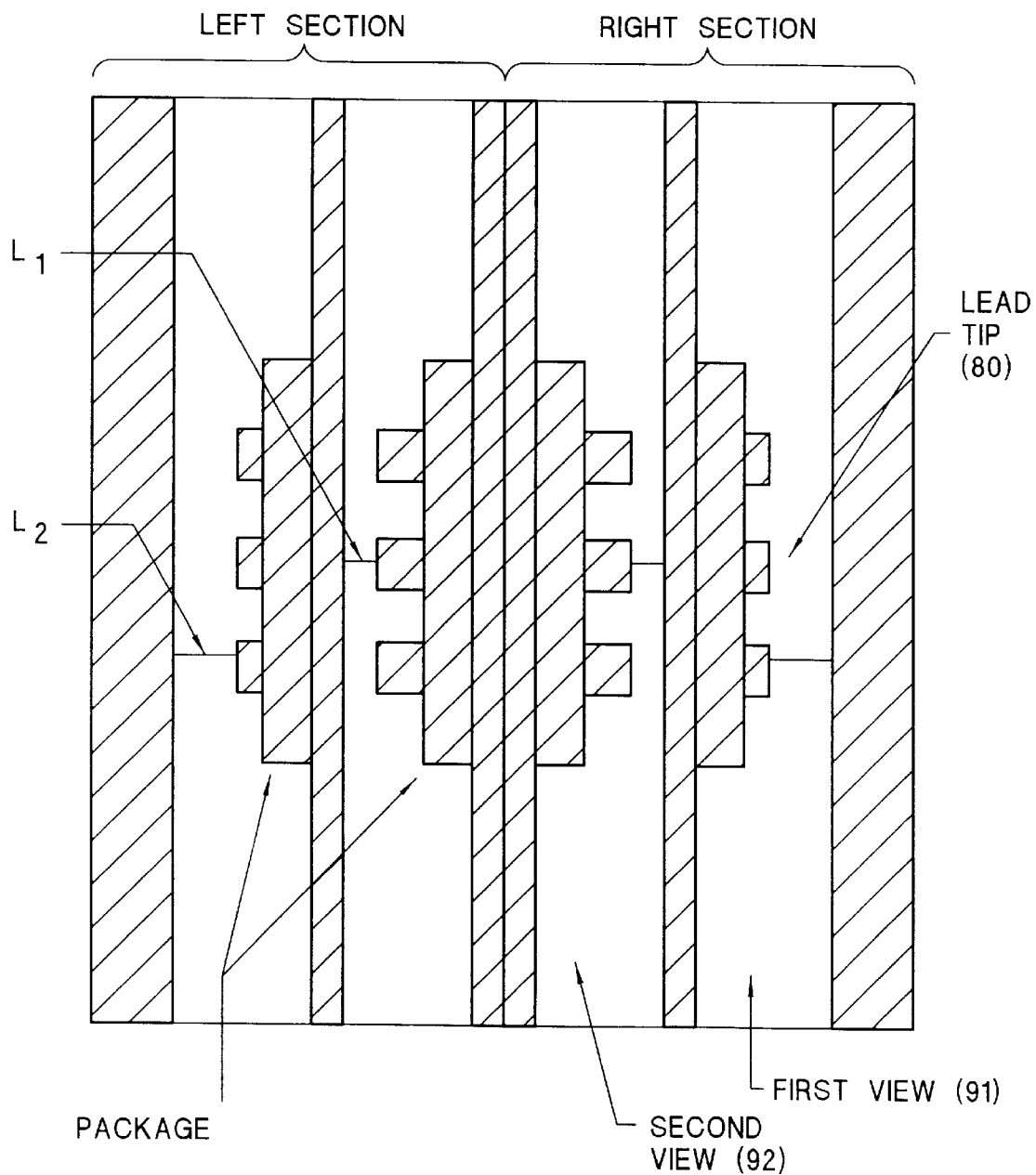
FIG. 3 illustrates an image of a low pin-count IC component captured by the optical inspection system of FIG. 1.

FIG. 3 illustrates the captured image, by the camera 60, of the dual-sided six-lead IC component 10. The image is divided into two sections: the left section of the image corresponds to the right side of the IC component 10; and the right section of the image corresponds to the left side of the IC 10 respectively. Each of the sections further consists of two subsections which correspond to the first and second optical paths 91, 92. For example, the outer subsection of the left section is imaged by light from the first optical path 91 and the inner subsection is imaged by light from the second optical path 92.

The system 11 captures the images, for example in gray scale, and digitizes the captured images for purposes of computation and analysis at very high speeds. The position of all the lead tips on the IC component 10 are precisely located by digital image processing means, such as edge detection means, using the computer that is connected to the camera 60. The system 11 also locates the datum edge 9 by edge detection means. Other features of the IC component 10 present in the captured image can be similarly located. These positions are subsequently correlated and analyzed by the computer for providing positional information in the form of X, Y, and Z coordinates with reference to the datum 1.

Figure 4:
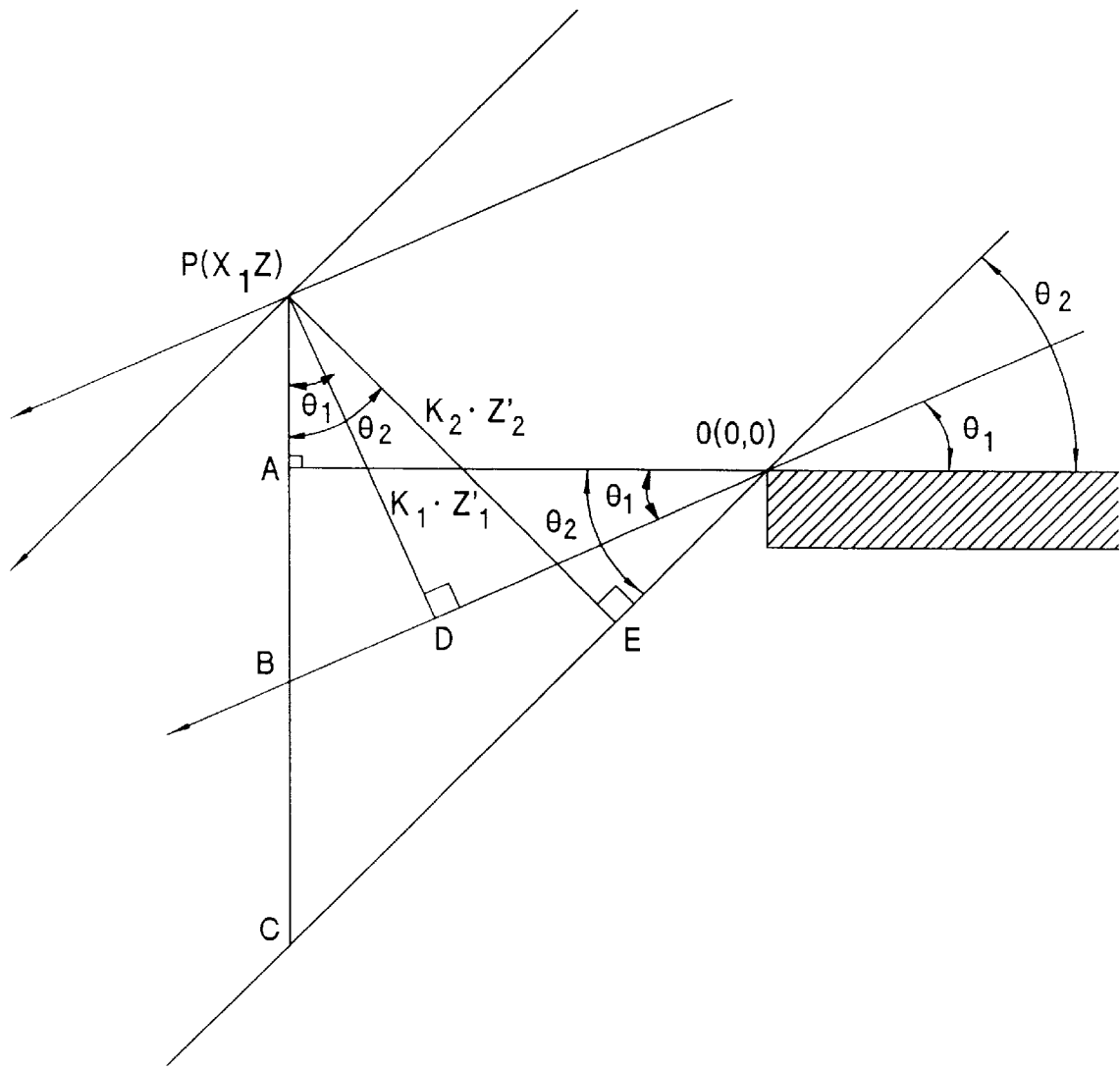
FIG. 4 illustrates the ray geometry to illustrate the mathematical analysis of the coordinates of a lead on the low pin-count IC component of FIG. 1.

A mathematical analysis for the derivation of the X, Y and Z coordinates of the tip of the lead 80 with reference to the datum edge 9 will now be provided. Reference is now also made to FIG. 4. The distance between the tip of the lead 80 and the datum edge 9 is measured from the captured image, and this is applied to both the image subsections of each image section. Let $L_1$ be the distance between the lead tip 80 and its associated datum edge 9 for the outer image subsection and $L_2$ be the distance between the same for inner image subsection. The datum edge 9 is denoted as point O. This point, O, is established as the origin (0, 0) for analysis purpose. A point on the tip of the lead 80 is denoted as P whose X and Z coordinates need to be determined. The first and second optical paths 91, 92 are inclined at angles $\theta_1$, $\theta_2$ with respect to the X-axis, which is also the horizontal axis 95 set by the datum 1. Angles $\theta_1$, $\theta_2$ are known once the system 11 is assembled and will not change during its operation. Since the two different optical paths 91, 92 pass through different optical elements before arriving at the camera 60, their magnification factors are different. However, these magnification factors will remain constant after the system 11 has been assembled. The magnification factor of the first optical path 91 is $K_1$ and the second optical path 92 is $K_2$.

It is therefore derived that:

$$Z = \frac{K_1 L_1 \sin\theta_2 - K_2 L_2 \sin\theta_2}{\sin(\theta_2 - \theta_1)}$$

$$X = \frac{K_2 L_2 \cos\theta_1 - K_1 L_1 \cos\theta_2}{\sin(\theta_2 - \theta_1)}$$

$L_1$ and $L_2$ are measured from the captured image as shown in FIG. 3. Hence, the coordinate (X, Z) of a point P can be determined with respect to the reference point O (0,0) on the datum 1. Furthermore, since the coordinate of Y is the same for both the datum 1 and the lead tip 80, the 3D coordinate is thus determined. This computation procedure is also applicable for determining the coordinates of other points on the IC component 10.

Figure 5:
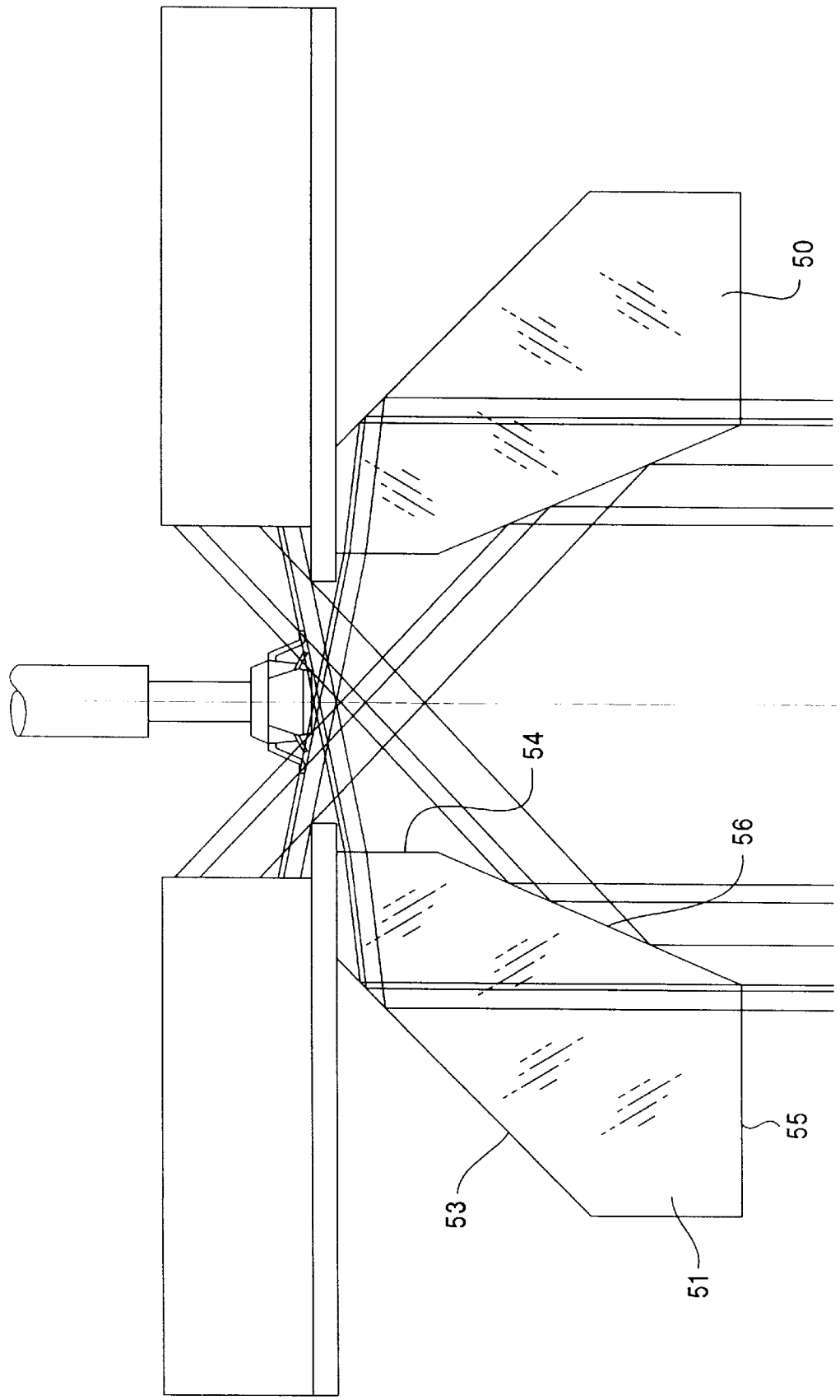
FIG. 5 illustrates a cross-section view of another optical inspection system according to an alternative embodiment of the invention.

The preferred embodiment may be modified in many ways. For example, the ways with which light along the first and second optical paths 91, 92 may be relayed to the camera 60 may be done with a pair of trapezoidal prisms 51, 52 as shown in FIG. 5. In place of the mirror 4, the system 11 may make use of a surface 53 on the trapezoidal prism 51 that operates in a total internal reflection mode for reflecting light rays along the optical path 91 entering the trapezoidal prism 51 through a surface 54. The light rays then exit the trapezoidal prism 51 through a surface 55. In addition, a surface 56 on the trapezoidal prism 51 is coated with reflective material, and light rays from the optical path 92 will be reflected at this surface 55 into the camera 60.

We claim:

1. An optical inspection apparatus for determining a position of an object with respect to a reference, comprising:
   a) a datum disposed in proximity to the object for providing the reference;
   b) a light source which provides light that impinges on a point on the object and a point on the datum to provide a pair of images of the object point and the datum point along first and second optical paths, wherein the first and second optical paths cross each other at an angle, and the object point and the datum point and the pair of images thereof along the first and second optical paths determine a plane;
   c) an imaging subsystem disposed along the first and second optical paths for capturing the pair of images, wherein the captured pair of images are subsequently correlated and analyzed to provide positional information of the object point with respect to the datum point.

2. The apparatus as in claim 1, wherein the imaging subsystem comprises a camera for capturing the pair of images, the camera having an optical axis.

3. The apparatus as in claim 2, wherein the imaging subsystem further comprises a reflector disposed in one of the first and second optical paths for relaying the one of the first and second optical paths so that it is substantially parallel with the other of the first and second optical paths.

4. The apparatus as in claim 3, wherein the optical axis of the camera is substantially parallel with the relayed one of the first and second optical paths and the other of the first and second optical paths.

5. The apparatus as in claim 2, wherein the imaging subsystem further comprises a first reflector disposed in the first optical path and a second reflector disposed in the second optical path for relaying the first and second optical paths so that they are substantially parallel with each other.

6. The apparatus as in claim 5, wherein the optical axis of the camera is substantially parallel with the relayed first and second optical paths.

7. The apparatus as in claim 6, wherein the first reflector is provided by a mirror.

8. The apparatus as in claim 7, wherein the second reflector is provided by the reflective surface of a prism operating in a total internal reflection mode, the prism having a substantially planar surface for receiving light, a substantially planar internal surface for internally-reflecting light, and a substantially planar surface for allowing reflected light to exit.

9. The apparatus as in claim 6, wherein the first and second reflectors are provided by the reflective surfaces of a prism operating in a total internal reflection mode, wherein the first reflector is provided by one of a substantially planar internal surface and a substantially planar external surface coated with a reflective substance, and the second reflector is formed by the other.

10. The apparatus as in claim 2, wherein the light source is disposed to provide back-light that impinges on the object point and the datum point to provide the pair of images of the object point and the datum point along the first and second optical paths by back-lighting.

11. An optical inspection method for determining a position of an object with respect to a reference, the method comprising the steps of:
   a) disposing a datum in proximity with the object to provide the reference;
   b) impinging light on a point on the object and a point on the datum to provide a pair of images of the object point and the data point along first and second optical paths, wherein the first and second optical paths cross each other at an angle and the object point and the datum point and the pair of images thereof along the first and second images optical paths determine a plane;
   c) capturing the pair of images;
   d) correlating and analyzing the captured pair of images to provide positional information of the object point with respect to the datum point.

12. The method as in claim 11, wherein the step of capturing the pair of images further includes using a camera to capture the pair of images, the camera having an optical axis.

13. The method as in claim 12, wherein the step of capturing the pair of images further includes relaying one of the first and second optical paths using a reflector so that the one of the first and second optical paths is substantially parallel with the other of the first and second optical paths.

14. The method as in claim 13, wherein the step of capturing the pair of images further includes disposing the camera such that the optical axis is substantially parallel with the relayed one of the first and second paths and the other of the first and second optical paths.

15. The method as in claim 12, wherein the step of capturing the pair of images further includes relaying the first and second optical paths using at least two reflectors so that the first and second optical paths are substantially parallel with each other.

16. The method as in claim 15, wherein the step of capturing the pair of images further includes disposing the camera such that the optical axis is substantially parallel with the relayed first and second paths.

17. The method as in claim 16, wherein the step of capturing the pair of images further includes using a mirror to provide a reflector for relaying the first optical path.

18. The method as in claim 17, wherein the step of capturing the pair of images further includes using a prism to provide a reflector for relaying the second optical path.

19. The method as in claim 16, wherein the step of capturing the pair of images further includes using a prism to provide the reflectors, the prism having a substantially planar internal surface and a substantially planar surface coated with a reflective substance for relaying the first and second optical paths.

20. The method as in claim 12, wherein the step of impinging light on the object point and the datum point further includes back-lighting the object point and the datum point to provide the pair of images of the object point and the data point along the first and second optical paths.

* * * * *

UNITED STATES PATENT AND TRADEMARK OFFICE
CERTIFICATE OF CORRECTION

PATENT NO. : 6,088,108  
DATED : July 11, 2000  
INVENTOR(S) : Peng-Seng Toh; Chiat-Pin Tay; Poh-Loy Chow; Peh-Kwan Han Page 1 of 1

It is certified that error appears in the above-identified patent and that said Letters Patent is hereby corrected as shown below:

<u>Column 6,</u>
Line 15, "data", should read -- datum --;
Line 19, "images" should be cancelled;
Line 63, "data", should read -- datum --.

Signed and Sealed this

Seventh Day of August, 2001

*Attest:*

Nicholas P. Godici

*Attesting Officer*

NICHOLAS P. GODICI
*Acting Director of the United States Patent and Trademark Office*